United States Patent
Rymer

(10) Patent No.: US 6,580,875 B2
(45) Date of Patent: Jun. 17, 2003

(54) EVAPORATOR DEVICE

(75) Inventor: Shaun Rymer, Beverley (GB)

(73) Assignee: Reckitt Benckiser (UK) Limited, Slough (GB)

(*) Notice: Subject to any disclaimer, the term of this patent is extended or adjusted under 35 U.S.C. 154(b) by 0 days.

(21) Appl. No.: 10/160,195

(22) Filed: Jun. 3, 2002

(65) Prior Publication Data

US 2003/0007787 A1 Jan. 9, 2003

Related U.S. Application Data

(63) Continuation of application No. PCT/GB00/04536, filed on Nov. 30, 2000.

(30) Foreign Application Priority Data

Dec. 4, 1999 (GB) ................................................ 9928593

(51) Int. Cl.⁷ .................................................. F24F 6/08
(52) U.S. Cl. ...................................... 392/395; 392/392
(58) Field of Search ................................ 392/386, 387, 392/390, 392, 394, 395; 122/366; 261/DIG. 65

(56) References Cited

U.S. PATENT DOCUMENTS

| | | | | |
|---|---|---|---|---|
| 5,647,053 A | * | 7/1997 | Schroeder et al. | .......... 392/390 |
| 6,278,840 B1 | * | 8/2001 | Basaganas Millan | ....... 392/390 |
| 6,285,830 B1 | * | 9/2001 | Basaganas Millan | ....... 392/395 |

FOREIGN PATENT DOCUMENTS

ES    U9002819 Y    1/1990

\* cited by examiner

*Primary Examiner*—Sang Paik
(74) *Attorney, Agent, or Firm*—Akin, Gump, Strauss, Hauer & Feld, L.L.P.

(57) ABSTRACT

A container for containing a liquid has a single opening through which extends a porous wick. The wick extends into the liquid. A portion of the wick extends out of the container through a tubular shield and a generally annular electric heater. The heater is movable between a first position, where the shield is disposed between the heater and the wick, and a second position, where the shield is not so disposed, so as to enable a supply of heat from the heater to the wick to be regulated.

9 Claims, 1 Drawing Sheet

EVAPORATOR DEVICE

CROSS-REFERENCE TO RELATED APPLICATION

This is a continuation of International Application No. PCT/GB00/04536, filed Nov. 30, 2000, which was published in the English language on Jun. 7, 2001, under International Publication No. WO 01/39809 A1, and the disclosure of which is incorporated herein by reference.

BACKGROUND OF THE INVENTION

The present invention relates to an evaporator device and particularly, although not exclusively, to an air freshener device.

One existing type of air freshener comprises a bottle, filled with a liquid perfume, which bottle is fitted with a wick, which extends out of the bottle. Heat is applied to the wick with an annular electrical heater causing the perfume to evaporate.

A problem with this type of air freshener is that it is not possible to regulate the rate of evaporation of perfume. A modified type of air freshener, which attempts to address this problem, is described in Spanish Utility Model U9002819Y. In this air freshener the annular heater is movable in a direction parallel to the axis of the wick, with the aim of controlling the amount of heat applied to the wick and, hence, the rate of evaporation of the perfume. However, in practice it has been found that this arrangement does not afford much regulation of the rate of evaporation. The output of the air freshener tends to be "all or nothing" with very little variation in between, depending upon whether the heater overlaps or is axially displaced from the wick.

BRIEF SUMMARY OF THE INVENTION

It is an object of the present invention to overcome, or at least mitigate, the above mentioned problems by providing an evaporator device which enables improved regulation of the rate of evaporation of liquid.

According to a first embodiment of the present invention there is provided an evaporator device adapted to receive a container for containing a liquid. The container is provided with a wick, part of which is disposed in the container and part of which extends outside of the container. The device is characterized in that it comprises a shield which partially covers the part of the wick which is outside of the container, when present, and a heater for heating the part of the wick which is outside of the container, when present. The heater is relatively movable between a first relative position, where the shield is disposed between the heater and wick, when present, and a second relative position, where the shield is not so disposed, so as to enable the supply of heat from the heater to the wick, when present, to be regulated.

According to a second embodiment of the present invention there is provided an evaporator device adapted to receive a container for containing a liquid. The container is provided with a wick, part of which is disposed in the container and part of which extends outside of the container, and a shield which partially covers the part of the wick which is outside of the container. The device is characterized in that it comprises a heater for heating the part of the wick which is outside of the container, when present. The heater is relatively movable between a first relative position, where the shield is disposed between the heater and wick, when present, and a second relative position, where the shield is not so disposed, so as to enable the supply of heat from the heater to the wick, when present, to be regulated.

According to a third embodiment of the present invention there is further provided an evaporator device comprising a container for containing a liquid, a wick, part of which is disposed in the container and part of which extends outside of the container, a heater for heating the part of the wick which is outside of the container, and a shield. The heater is relatively movable between a first relative position, where the shield is disposed between the heater and wick, and a second relative position, where the shield is not so disposed, so as to enable the supply of heat from the heater to the wick to be regulated.

The evaporator device is preferably used to evaporate an active agent in liquid form.

Suitable solvents for the active agent include water, alkyl alcohol, e.g., isopropanol or ethanol, an ether (such as monopropylene glycol methyl ether, dipropylene glycol methyl ether and/or tripropylene glycol methyl ether), carbitol, a glycol (such as propylene glycol or dipropylene glycol).

The active agent preferably comprises a perfume and, optionally, a malodor counteractant and/or an insecticide.

A suitable perfume for use in the invention comprises one or more fragrant materials, such as cedarwood oil, sandalwood oil, bergamot, Bulgarian rose oil, patchouli, myrrh, clove leaf oil, linalol, ethyl alcohol, terpineol, menthol, citronellal, and/or phenyl ethyl alcohol.

A suitable deodorant for use in the invention is one or more aroma and/or non-aroma chemicals which are known to have an action in reducing the perception of the intensity of malodors, e.g., unsaturated esters, ketones, aldehydes, and/or a fragrant material, e.g., citronellal and/or cedarwood oil (which is known to counteract the perception of tobacco malodor).

A suitable insecticide for use in the invention comprises one or more of the natural insecticides, such as a pyrethroid, nicotinoid, rotenoid, and/or one or more of the synthetic insecticides, e.g., tetramethrin, bioallethrin, allethrin, phenthrin, a dinitrophenol, an organothiocyanate, benzene hexachloride, a polychlorinated cyclic hydrocarbon (e.g., heptachlor, aldrin and/or telodrin), and/or an organophosphorous (e.g., tetraethyl pyrophosphate).

The active agent may further comprise an antioxidant, such as tocopherol, ascorbyl palmitate, butylated toluene, ascorbic acid, tert-butyl hydroquinone, beta-carotene, and/or a gallate. In addition, the active agent may optionally comprise a UV stabilizer, such as Uvinol™ 400.

A suitable container for the liquid is one made from a water/organic solvent-insoluble material, which is optionally either a plastic material, for example, polypropylene, HDPE (high density polyethylene), PET (polyethylene terephthalate), or Barex™ or, preferably, glass A. Suitable wick is made, for example, from a natural or synthetic fibrous material, such as cotton, fiberglass, mineral fibers, cellulose, ceramic, graphite or polyester.

The shield is preferably arranged such that it surrounds a portion of the exposed part of the wick, when present. As such, it is preferred that the shield is in the form of a tube through which a portion of the exposed part of the wick may extend. The shield is preferably substantially annular in cross-section, although other configurations may be employed.

The heater is preferably generally annular, defining an aperture. It is preferably arranged to be movable in a direction generally parallel to the axis of the wick, when present. When a container provided with a wick is inserted into the device, the wick preferably extends through the aperture defined by the heater.

Where the shield comprises a tube, through which a portion of the wick extends when present, the aperture through the heater is preferably of sufficient size to enable the heater to pass over the shield. As such, it will be appreciated that the wick, shield and heater can be arranged so that the heater may be moved along the axis of the wick. Thus, at one position the shield lies between the heater and wick, reducing the heat flow from the heater to the wick, and at another position the heater is directly exposed to the wick to obtain maximum heat flow to the wick. In intermediate positions, the heater is partially shielded from the wick allowing the flow of heat to be regulated between the two extremes.

In order to afford even greater regulation of the amount of heat supplied to the wick, the thickness of the shield preferably varies in the direction in which relative movement of the heater can be made. The thinner the shield, the more heat it will transmit and vice versa. The thickness of the shield could vary continuously to enable continuous variation of heat flow to the wick, or alternatively it could vary in steps to give a number of discrete levels.

The heater is preferably an electrical element formed into a ring shape, for example a torroidally wound resistor wire or a P.T.C. element. The heater may be encased in a plastic material. The heat output of the heating means is preferably suitable to give a running temperature of from about 50 to about 120° C., more preferably from about 60 to about 80° C., most preferably about 70° C.

The device according to the invention is preferably an electrical device. The electrical power supply is optionally either in the form of batteries or, preferably, the electrical device is adapted to be connected to an electrical power supply, e.g., a domestic mains socket.

Preferably, the device comprises a housing which is adapted to support the heater, the housing preferably including one or more apertures to allow the perfume or other vapor to escape. The housing is preferably formed from a plastic material, for example polypropylene.

In one arrangement the device and, particularly, the housing comprise the shield. Preferably, the shield is formed integrally with the housing. This arrangement has the advantage of being economical to manufacture, as no separate component is required.

In another arrangement the shield is formed separately, for example as part of the container.

Preferably, the shield forms part of a plug for retaining the wick in the container. This arrangement allows the shield to be formed from a different material than the remainder of the device. This would allow the wick to be formed from a heat insulating material to give improved control over the flow of heat, rather than being restricted to the material from which the housing is constructed.

Preferably, the device is provided with an external control, which regulates the relative movement of the heater. This is in order that the user is able to adjust the rate of evaporation of liquid. The control may, for example, comprise a wheel, which may optionally be graduated. The device according to the invention is preferably provided with an actuating means, e.g. a switch, to control operation of the device. More preferably, this actuating means forms part of the external control.

The provision of a shield, particularly one of varying thickness, enables improved control over the flow of heat from the heater to wick, and hence over the rate of evaporation of liquid, compared to known devices. The invention allows the user to adjust the vapor output of the device progressively between a maximum and minimum level, for example depending on the size of the room in which the device is installed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
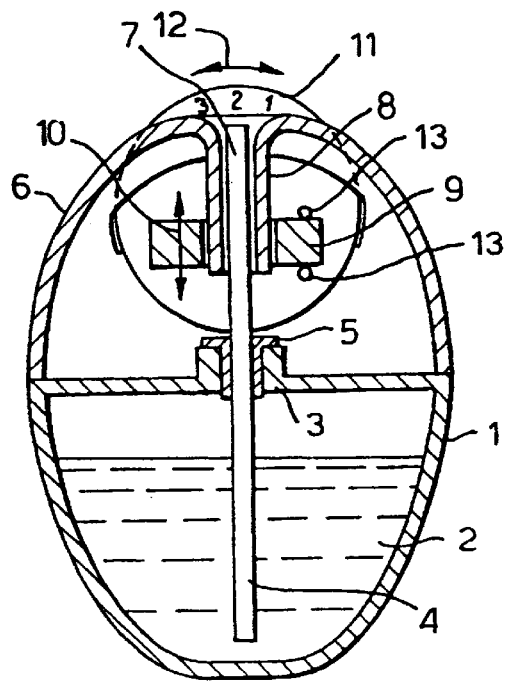
FIG. 1 is a diagrammatic cross-sectional view of an evaporator device according to the invention.

Referring to FIG. 1, an evaporator device comprises a container 1 for containing a liquid 2, for example a perfume. The container 1 is formed from a plastic material, for example polypropylene. The container has a single opening 3 through which there extends a porous wick 4, which is retained in position by a plug 5, which fits snugly into the opening 3. The wick 4 extends into the liquid 2, which is absorbed by the wick 4 and diffuses along its length.

The wick 4 extends into a region generally defined by a top cover 6 of the device. The top cover 6 is also formed from a plastic material, for example polypropylene. The top cover 6 engages with the container 1 with a snap fit, although any other suitable technique could be used, for example using an adhesive or screw fastening. The top cover 6 includes apertures (not shown) to enable vapor from the wick 4 to escape.

The portion of the wick 4 which extends out of the container 1 and indicated generally by reference numeral 7 extends through both a tubular shield 8 and a generally annular electrical heater 9.

The shield 8 is generally annular in cross-section and surrounds the wick 4. The shield is formed integrally with the top cover 6, from the same material.

The heater 9 may be produced from any suitable components, although a P.T.C. heater connected to a metal alloy and encased in a plastic material is preferred.

The heater 9 is mounted movably on the device to enable it to move in a direction substantially parallel to the axis of the wick 4, as shown by the arrow 10.

Movement of the heater is effected by an adjuster wheel 1, which is rotatably mounted on the device and may be moved as indicated by arrow 12. The adjuster wheel 11 includes two projections 13 between which the heater 9 is received. It will be appreciated therefore that rotation of the wheel 11 will result in movement of the heater along a direction substantially parallel to the axis of the wick.

The adjuster wheel 11 is partially exposed through the top cover 6 to enable adjustment of the position of heater 9 from the outside of the device. The wheel is marked with numbers to indicate the rate of vaporization selected. Other markings could, of course, be employed. The periphery of the wheel is knurled.

When the heater 9 is moved in a direction toward the top cover 6, away from the container 1, it will pass over the shield 8. When the shield 8 lies between the heater 9 and wick 4, it will reduce the amount of heat transmitted from the heater 9 to wick 4 to a minimum and so reduce the rate of evaporation of liquid from the wick 4.

When the heater 9 is moved in the opposite direction, it can pass beyond the end of the shield 8, so that there is no obstruction to the passage of heat from the heater 9 to the wick 4. This leads to maximum transfer of heat to the wick 4 and hence maximizes the rate of evaporation of liquid from the wick 4.

If the heater 9 is moved to a position between those described above, then it will be partially shielded from and partially exposed to the wick 4. This will result in the rate of heat transfer to the wick 4 being somewhere between the maximum, when the heater 9 is fully exposed, and minimum, where the heater 9 is fully shielded, rates of heat transfer. The rate of heating of the wick 4, and hence the rate of evaporation of liquid, can be varied progressively between a maximum and a minimum value. This has not been possible with existing devices.

Figure 2:
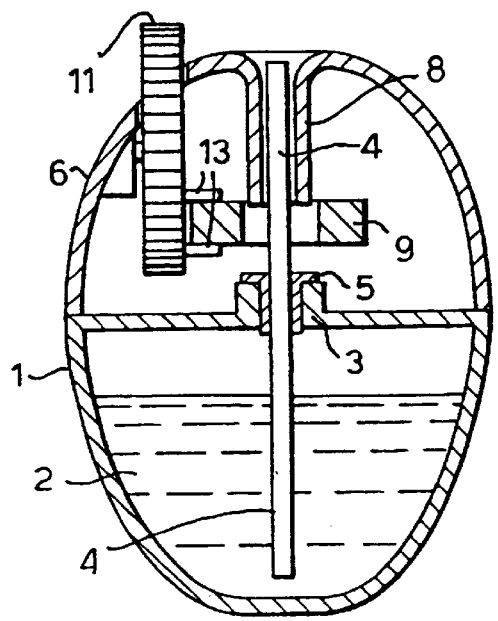
FIG. 2 is a cross-sectional view of a part of a device similar to that illustrated in FIG. 1 taken at right angles to the cross-section of FIG. 1 to show details of the adjuster wheel.

The mechanism by which the heater may be moved is also illustrated in FIG. 2. The same reference numerals are used in FIG. 2 to identify similar components to those of the device illustrated in FIG. 1.

Figure 3:
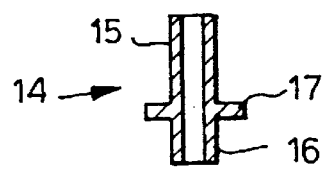
FIG. 3 is a longitudinal sectional view of an alternative form of plug for use in an evaporator device of the invention.

In an alternative embodiment of the device illustrated in FIG. 1, the shield could be provided as an extension of the plug 5 rather than the top cover 6. A suitable alternative plug 14 is illustrated in cross-section in FIG. 3, the plug comprising a shield 15, a portion 16 for engaging an opening 3, and a flange 17 to restrict insertion of the plug into an opening. If the plug 14 were substituted for the plug 5 shown in FIG. 1, then it would be necessary to remove the shield 8.

In this arrangement it will be appreciated that when the heater 9 is moved towards the container 1, the shield 15 will be disposed between the heater 9 and the wick 4 to give a minimum rate of evaporation, and when the heater 9 is moved toward the cover 6, then there will be no shielding and a maximum rate of evaporation will be obtained.

An advantage of this arrangement is that the plug 14, with shield 15, may be formed from a different material than the top cover 6. For instance, to achieve a low minimum rate of evaporation, it may be desirable for the shield to be formed from a material with good thermal insulating properties and possibly also heat reflective properties. To make the whole top cover 6 from such a material could be inconvenient or expensive compared to producing only the plug 14 from such a material.

In another alternative arrangement the shield, whether part of the top cover, plug or another component, is of varying thickness to allow different rates of heat flow from the heater to the wick, depending upon the relative positions of the heater and the shield.

Figure 4:
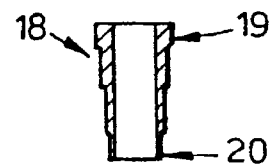
FIG. 4 is a longitudinal sectional view of an alternative form of shield for use in an evaporator device of the invention.

An example of a shield of varying thickness is illustrated in cross-section in FIG. 4. The shield 18 has four discrete regions of different thickness. The wall thicknesses at these regions are 2, 1.5, 1 and 0.5 mm. The thicker the shield the more effectively it will reduce heat transfer from the heater to the wick. Therefore, when the heater is adjacent to the thicker end 19 of the shield 18, less heat will be transmitted to a wick extending through the shield than when it is adjacent to the thinner end 20 of the shield.

The provision of a shield of varying thickness allows even greater and more progressive control of the amount of heat transmitted to the wick and therefore the rate of evaporation of liquid. The shield could be of continuously varying thickness, rather than having discrete steps.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An evaporator device adapted to receive a container for containing a liquid to be evaporated, the container having a wick having a first part disposed in the container and a second part extending outside of the container, the device comprising a shield which partially covers the second part of the wick, and a heater for heating the second part of the wick, when present, the heater being relatively movable between a first relative position where the shield is disposed between the heater and the wick, when present, and a second relative position where the shield is not so disposed, so as to enable a supply of heat from the heater to the wick, when present, to be regulated.

2. The device according to claim 1, wherein a thickness of the shield varies in a direction of relative movement of the heater.

3. The device according to claim 1, further comprising a control which is operable from outside the device to regulate the relative movement of the heater.

4. An evaporator device adapted to receive a container for containing a liquid to be evaporated, the container having a wick having a first part disposed in the container and a second part extending outside of the container, a shield partially covering the second part of the wick, the device comprising a heater for heating the second part of the wick, when present, the heater being relatively movable between a first relative position where the shield is disposed between the heater and the wick, when present, and a second relative position where the shield is not so disposed, so as to enable a supply of heat from the heater to the wick, when present, to be regulated.

5. The device according to claim 4, wherein a thickness of the shield varies in a direction of relative movement of the heater.

6. The device according to claim 4, further comprising a control which is operable from outside the device to regulate the relative movement of the heater.

7. An evaporator device comprising a container for containing a liquid, a wick having a first part disposed in the container and a second part extending outside of the container, a heater for heating the second part of the wick, and a shield, wherein the heater is relatively movable between a first relative position where the shield is disposed between the heater and wick and a second relative position where the shield is not so disposed, so as to enable a supply of heat from the heater to the wick to be regulated.

8. The device according to claim 7, wherein a thickness of the shield varies in a direction of relative movement of the heater.

9. The device according to claim 7, further comprising a control which is operable from outside the device to regulate the relative movement of the heater.

* * * * *